(12) United States Patent
Wu et al.

(10) Patent No.: US 9,328,147 B2
(45) Date of Patent: May 3, 2016

(54) RECOMBINANT BACULOVIRUS VECTOR AND USES THEREOF

(71) Applicant: Chung Yuan Christian University, Jhongli, Taoyuan County (TW)

(72) Inventors: Tzong-Yuan Wu, Panchiao (TW); Mean-Shine Chen, Jhongli (TW); Chao-Yi Teng, Jhongli (TW); Ying-Ju Chen, PingTung County (TW)

(73) Assignee: CHUNG YUAN CHRISTIAN UNIVERSITY, Jhongli, Taoyuan County (TW)

( * ) Notice: Subject to any disclaimer, the term of this patent is extended or adjusted under 35 U.S.C. 154(b) by 0 days.

(21) Appl. No.: 14/478,870

(22) Filed: Sep. 5, 2014

(65) Prior Publication Data

US 2016/0068575 A1 Mar. 10, 2016

(51) Int. Cl.
*A61K 39/12* (2006.01)
*C12N 7/00* (2006.01)
*C07K 14/005* (2006.01)
*A61K 39/00* (2006.01)

(52) U.S. Cl.
CPC ............... *C07K 14/005* (2013.01); *C12N 7/00* (2013.01); *A61K 39/00* (2013.01); *A61K 2039/70* (2013.01); *C12N 2710/14043* (2013.01); *C12N 2750/10034* (2013.01); *C12N 2770/24334* (2013.01)

(58) Field of Classification Search
None
See application file for complete search history.

(56) References Cited

U.S. PATENT DOCUMENTS 7,829,101 B2 * 11/2010 Eichmeyer ............. A61K 33/00
424/204.1

OTHER PUBLICATIONS

Wu et al. (Journal of Applied Microbiology. 2008; 104: 1354-1362).*
Xu et al. (Vaccine. 2008; 26: 5455-5460).*
Seq ID No. 5 sequence alignment with GenEmbl access No. AF323747 (Apr. 2002).*
Seq ID No. 6 sequence alignment with Geneseq access No. AZM32758 (Oct. 2011).*
Seq ID No. 7 sequence alignment with Geneseq database access No. ADT75788 (Jan. 2005).*

* cited by examiner

*Primary Examiner* — Shanon A Foley
(74) *Attorney, Agent, or Firm* — Muncy, Geissler, Olds & Lowe, P.C.

(57) ABSTRACT

Disclosed herein is a recombinant viral construct and its uses thereof. The recombinant viral construct is capable of simultaneously expressing three exogenous proteins, including a classical swine fever virus (CSFV) antigen, a porcine *circovirus* type 2 (PCV2) antigen, and an immunomodulatory protein. The recombinant viral construct is hence useful as a bio-tool for simultaneously producing multiple antigens of a bi-subunit vaccine.

13 Claims, 8 Drawing Sheets
(2 of 8 Drawing Sheet(s) Filed in Color)

Fig. 1

| | GFP | Bright field |
|---|---|---|
| vAc-E2-PnV339-E-Rhir-mcsII | | |
| vAc-PCV2-PnV339-E-Rhir-mcsII | | |
| vAc-E2-PnV339-E-Rhir-FVE | | |
| vAc-E2-2A-PCV2-PnV339-E-Rhir-FVE | | |

Anti-CSFV-E2 antibody in Balb/C mice

RECOMBINANT BACULOVIRUS VECTOR AND USES THEREOF

BACKGROUND OF THE INVENTION

1. Field of the Invention

The present disclosure relates to a novel recombinant viral construct. More particularly, the present disclosure relates to a recombinant viral construct and its uses in producing multiple antigenic proteins required for manufacturing a multi-subunit (e.g., a bi-subunit) vaccine.

2. Description of Related Art

Classical swine fever (CSF) is a contagious and often fatal disease of swine, characterized by fever, hemorrhages, ataxia and immunosuppression. The causative agent is classical swine fever virus (CSFV), a member of the genus *Pestivirus* of the family Flaviviridae. In many countries, the virus is not endemic, but outbreaks of CSF occur periodically, and may cause large economic losses. Consequently, it is necessary to develop efficient vaccines against CSFV so as to protect pigs against clinical signs of CSF and possible spread of CSFV. A vaccine directed to the structure glycoprotein E2 of CSFV has the advantageous protecting effect on pigs and is known to induce a neutralizing antibody response in pigs.

Post-weaning multi-systemic wasting syndrome (PMWS) is another contagious disease affecting pigs worldwide. This syndrome causes considerable economic losses due to high mortality rates and reduced feed conversion efficiency in weaning and fattening pigs. Porcine *circovirus* type 2 (PCV2), belonging to the genus *Circovirus* of the family of Circoviridae, is regarded as the etiological agent of PMWS. Various PCV2 vaccines have been shown to be effective against the development of PMWS, and their use resulted in a significant improvement of nursery and mortality rates of vaccinated farms. Among the known PCV2 vaccines, vaccines directed to open reading frame-2 (ORF-2), which is a major immunogenic protein produced by PCV2, exhibit superior protection effect on pigs due to the production of the PCV2-specific neutralizing antibodies.

As described above, though there are vaccines directed to either CSFV or PCV2, yet most of them are mono-subunit vaccines, meaning each vaccine contains just one type of antigenic protein, either CSFV or PCV2 antigen. Such mono-subunit vaccine can only protect the animal from one type of virus, and thus limiting its protecting spectrum and efficacy.

Accordingly, there exists in the related art a need of a multi-subunit vaccine, which encompasses more than one antigens so as to protect porcine from various viral infections.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, disclosure herein features a recombinant viral construct capable of simultaneously expressing three exogenous proteins, which include a CSFV antigen or a fragment thereof, a PCV2 antigen or a fragment thereof, and an immunomodulatory protein or a fragment thereof; and the use of the recombinant viral construct in producing at least two antigens and a modulatory protein for packaging into a bi-subunit vaccine.

One aspect of the present disclosure is directed to a recombinant viral construct for producing a bi-subunit vaccine. The recombinant viral construct comprises:

(1) a promoter;

(2) a first expression cassette, operably linked to the promoter, wherein the first expression cassette comprises in sequence, a first nucleic acid encoding a CSFV antigen or a fragment thereof, a self-cleaving element encoding a self-cleaving peptide, and a second nucleic acid encoding a PCV2 antigen or a fragment thereof;

(3) a second expression cassette, operably linked to the promoter, wherein the second expression cassette comprises in sequence, a first internal ribosomal entry site (IRES) element or a portion thereof, and a third nucleic acid encoding a reporter polypeptide; and (4) a third expression cassette, operably linked to the promoter, wherein the third expression cassette comprises in sequence, a second IRES element or a portion thereof, and a fourth nucleic acid encoding an immunomodulatory polypeptide or a portion thereof.

According to some embodiments of the present disclosure, the promoter is any of a polyhedrin (polh) promoter, a baculovirus-derived promoter, a *Bombyx mori*-derived actin promoter, a cytomegalovirus (CMV) promoter, or a chicken β-actin promoter combined with a CMV enhancer (CAG promoter). In some embodiments of the present disclosure, the baculovirus-derived promoter is any of an immediate-early1 (IE1) promoter, an IE2 promoter, a p6.9 promoter, a VP39 promoter, or a p10 promoter.

In some embodiments of the present disclosure, the CSFV antigen is a CSFV-E2 antigen having an amino acid sequence at least 90% identical to SEQ ID NO: 1.

In some embodiments of the present disclosure, the PCV2 antigen is a PCV2 open reading frame 2 (ORF-2) antigen having an amino acid sequence at least 90% identical to SEQ ID NO: 2.

According to some embodiments of the present disclosure, the self-cleaving peptide is selected from the group consisting of a nuclear inclusion protein a (Nia) protease, a P1 protease, a 3C protease, a L protease, a 2A protease, a 3C-like protease, and a 2A-like protease. In some embodiments of the present disclosure, the self-cleaving peptide is the 2A-like protease, which contains a canonical motif of Asp-X-Glu-X-Asn-Pro-Gly-Pro, and the self-cleaving site is located between the glycine and proline residues. In one preferred embodiment of the present disclosure, the self-cleaving peptide is the 2A-like protease isolated from *Perina nuda* virus (PnV) and has an amino acid sequence of SEQ ID NO: 3. In another preferred embodiment of the present disclosure, the self-cleaving peptide is the 2A-like protease isolated from PnV and has an amino acid sequence of SEQ ID NO: 4.

According to some embodiments of the present disclosure, each of the first and second IRES elements is derived or modified from a portion of 5' untranslated region (5'-UTR) of a virus, which is any of PnV, *Rhopalosiphum padi* virus (RhPV), Aphid lethal paralysis virus, Black queen cell virus, Cricket paralysis virus, *drosophila* C virus, *Himetobi P* virus, *Homalodisca coagulata* virus-I, Kashmir bee virus, *Plautia stali* intestine virus, *Solenopsis invicta* virus-1, Taura syndrome virus, Encephalomyocarditis virus, or Hepatitis C virus. In some preferred embodiments of the present disclosure, each of the first and second IRES elements is the PnV IRES having a nucleotide sequence of SEQ ID NO: 5. In other preferred embodiments of the present disclosure, each of the first and second IRES elements is the RhPV IRES having a nucleotide sequence of SEQ ID NO: 6. The first and second IRES elements are not necessary to be the same.

According to some embodiments of the present disclosure, the reporter polypeptide is selected from the group consisting of green fluorescence protein (GFPs), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), and *Clavularia* fluorescent protein (cFP).

According to some embodiments of the present disclosure, the immunomodulatory polypeptide is any of fungal immunomodulatory protein *Flammunlina velutipes* (FIP-FVE), fungal immunomodulatory protein Ganodera *tsugae* (FIP-GTS), fungal immunomodulatory protein *Volvariella volvacea* (FIP-VVO), *Ganoderma lucidum* Ling-Zhi-8 (LZ-8), fungal immunomodulatory protein *Ganoderma microsporum* (GMI), or immunomodulatory Protein *Tremella FuciFormis* (TFP). In some embodiments of the present disclosure, the immunomodulatory polypeptide is FIP-FVE having an amino acid sequence at least 90% identical to SEQ ID NO: 7.

According to some embodiments of the present disclosure, the recombinant viral construct is derived from a virus, which is selected from the group consisting of baculovirus, adenovirus, adeno-associated virus, retrovirus, lentivirus, sindbis virus, herpes simplex virus, semliki forest virus, and poxvirus.

In another aspect, the present disclosure provides a bi-subunit vaccine, which comprises, a first effective amount of a CSFV antigen or a fragment thereof, a second effective amount of a PCV2 antigen or a fragment thereof, a third effective amount of an immunomodulatory polypeptide or a portion thereof, and a pharmaceutically acceptable adjuvant.

In some preferred embodiments of the present disclosure, the CSFV antigen is a CSFV-E2 antigen, the PCV2 antigen is a PCV2-ORF2 antigen, and the immunomodulatory polypeptide is a FIP-FVE protein.

Many of the attendant features and advantages of the present disclosure will become better understood with reference to the following detail description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

"Nucleotide sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

As used herein, the term "immunomodulatory" means that an agent, e.g., a protein or peptide, is capable of enhancing a humoral and/or cellular immune response, e.g., a cytotoxic T cell response or a T helper cell response, when administered to an animal having an immune system. An immunomodulatory protein includes any protein or active portion thereof, having the ability to induce, enhance, or extend the immune response of a subject.

The term "an effective amount" used herein refers to a dose sufficient to provide concentrations high enough to generate (or contribute to the generation of) an immune response in the subject thereof. An effective amount can be administered in one or more administrations, applications or dosages.

The term "adjuvant" used herein refers to a compound or molecule that augments the subject's immune response to an antigen when administered with that antigen. Adjuvant-mediated enhancement and/or extension of the duration of the antigen-specific immune response can be assessed by any method known in the art including, without limitation, an increase in a humoral or cellular immune response, e.g., a cytotoxic T cell or helper T cell immune response.

The practices of this invention are herein after described in detail with respect to a novel recombinant viral construct capable of simultaneously expressing three exogenous proteins, which are CSFV antigen or a fragment thereof, PCV2 antigen or a fragment thereof, and immunomodulatory protein or a fragment thereof. This recombinant viral construct is thus useful as a means for producing a bi-subunit vaccine.

One aspect of the present disclosure is therefore directed to a recombinant viral construct for producing a bi-subunit vaccine. The recombinant viral construct comprises:

(1) a promoter;

(2) a first expression cassette, operably linked to the promoter, wherein the first expression cassette comprises in sequence, a first nucleic acid encoding a CSFV antigen or a fragment thereof, a self-cleaving element encoding a self-cleaving peptide, and a second nucleic acid encoding a PCV2 antigen or a fragment thereof;

(3) a second expression cassette, operably linked to the promoter, wherein the second expression cassette comprises in sequence, a first IRES element or a portion thereof, and a third nucleic acid encoding a reporter polypeptide; and (4) a third expression cassette, operably linked to the promoter, wherein the third expression cassette comprises in sequence, a second IRES element or a portion thereof, and a fourth nucleic acid encoding an immunomodulatory polypeptide or a portion thereof.

To produce multiple antigens suitable for packaging into the bi-subunit vaccine of the present disclosure, three expression cassettes are independently constructed and operably linked to a promoter of a viral vector, and thereby generating a recombinant viral vector capable of expressing at least three exogenous proteins (e.g., two antigens and one immunomodulatory protein) simultaneously in a host.

The first expression cassette is constructed to comprise in sequence, a first nucleic acid encoding a CSFV antigen or a fragment thereof, a self-cleaving element encoding a self-cleaving peptide, and a second nucleic acid encoding a PCV2 antigen or a fragment thereof. In embodiments of the present disclosure, the CSFV antigen is a CSFV-E2 antigen derived from the structure glycoprotein E2 of CSFV genome and has an amino acid sequence at least 90% identical to SEQ ID NO: 1. In embodiments of the present disclosure, the PCV2 antigen is a PCV2-ORF2 antigen derived from ORF2 of PCV2 genome and has an amino acid sequence at least 90% identical to SEQ ID NO: 2. The CSFV-E2 and the PCV-ORF-2 antigens are connected by a self-cleaving peptide, so that the two antigens are initially expressed as a single protein. The thus generated single protein is then self-cleaved by the self-protease activity of the self-cleaving peptide situated between the two antigens, and thereby releasing the two antigens (i.e., CSFV-E2 and PCV2-ORF2) from the expressed single protein.

According to some embodiments of the present disclosure, the self-cleaving peptide may be selected from the group consisting of Nia protease and P1 protease of potyvirus; 3C protease and L protease of aphthovirus; 2A protease and 3C protease of enterovirus; 2A protease and 3C protease of rhinovirus; 2A protease and 3C protease of picornavirus; 3C-like protease of rice tungro spherical virus (RTSV); and 2A-like protease. In some embodiments of the present disclosure, the self-cleaving peptide is the 2A-like protease, which contains a canonical motif of Asp-X-Glu-X-Asn-Pro-Gly-Pro, and the self-cleaving site is located between the glycine and proline residues. In the preferred embodiment of the present disclosure, the self-cleaving peptide is the 2A-like protease of PnV having an amino acid sequence of SEQ ID NO: 3. In another preferred embodiment of the present disclosure, the self-cleaving peptide is the 2A-like protease of PnV having an amino acid sequence of SEQ ID NO: 4.

The second expression cassette is constructed to comprise in sequence, a first IRES element or a portion thereof, and a third nucleic acid encoding a reporter polypeptide. The IRES element is a nucleic acid that allows translation initiation in the middle of a messenger RNA sequence and thus usually employed in the bi-cistronic or multi-cistronic expression system to simultaneously but independently express two or more proteins from the same RNA transcript. Several IRES elements have been discovered from viruses, where they serve as a means to ensure the viral translation is active during times when host translation is inhibited. The first IRES element used to mediate the expression of the reporter polypeptide may be derived or modified from a portion of 5'-UTR of a virus, which is any of PnV, RhPV, Aphid lethal paralysis virus, Black queen cell virus, Cricket paralysis virus, *drosophila* C virus, *Himetobi* P virus, *Homalodisca coagulata* virus-I, Kashmir bee virus, *Plautia stali* intestine virus, *Solenopsis invicta* virus-1, Taura syndrome virus, Encephalomyocarditis virus, or Hepatitis C virus. According to some embodiments of the present disclosure, the first IRES element is the PnV IRES having a nucleotide sequence of SEQ ID NO: 5. According to other embodiments of the present disclosure, the first IRES element is the RhPV IRES having a nucleotide sequence of SEQ ID NO: 6.

The reporter polypeptide used herein is for monitoring the expression of exogenous proteins and facilitating subsequent viral purification. Suitable reporter polypeptides for use in the present disclosure include, but are not limited to, GFP, EGFP, DsRed, BFP, EYFP, amFP, zFP, dsFP, and cFP. In some preferred embodiments of the present disclosure, the reporter polypeptide is EGFP.

The third expression cassette is constructed to comprise in sequence, a second IRES element or a portion thereof, and a fourth nucleic acid encoding an immunomodulatory polypeptide or a portion thereof. With the similar concept as illustrated above, the second IRES element is used to mediate the expression of the immunomodulatory polypeptide, and may also be derived or modified from a portion of 5'-UTR of a virus, which is any of PnV, RhPV, Aphid lethal paralysis virus, Black queen cell virus, Cricket paralysis virus, *drosophila* C virus, *Himetobi* P virus, *Homalod iscacoagulata* virus-I, Kashmir bee virus, *Plautia stall* intestine virus, *Solenopsis invicta* virus-1, Taura syndrome virus, Encephalomyocarditis virus, or Hepatitis C virus. According to some embodiments of the present disclosure, the second IRES element is the PnV IRES having a nucleotide sequence of SEQ ID NO: 5. According to other embodiments of the present disclosure, the second IRES element is the RhPV IRES having a nucleotide sequence of SEQ ID NO: 6.

It is noted that the first IRES element of the second expression cassette and the second IRES element of the third expression cassette are not necessary to be the same. In certain embodiments of the present disclosure, the first IRES element is the PnV IRES, while the second IRES element is the RhPV IRES.

Since an immunomodulatory protein functions as an adjuvant to augment the immune response stimulated with antigens, thus an immunomodulatory protein was constructed into the third expression cassette, so that the expression of this immunomodulatory protein may enhance the vaccine efficacy against CSFV and PCV2. Suitable immunomodulatory polypeptides for use in the present disclosure conclude, but are not limited to, FIP-FVE, FIP-GTS, FIP-VVO, LZ-8, GMI, and TFP. In some embodiments of the present disclosure, the immunomodulatory polypeptide is FIP-FVE having an amino acid sequence at least 90% identical to SEQ ID NO: 7.

The afore-mentioned three expression cassettes are independently linked to a promoter of a viral vector, to produce the recombinant viral construct of the present disclosure. Suitable viral vectors for use in the present disclosure include, but are not limited to, vectors that derived from baculovirus, adenovirus, adeno-associated virus, retrovirus, lentivirus, sindbis virus, herpes simplex virus, semliki forest virus, and poxvirus. In some preferred of the present disclosure, the recombinant viral construct is derived from baculovirus. Promoters suitable for use in the present disclosure include, but are not limited to, polh promoter, baculovirus-derived promoters, *Bombyx mori*-derived actin promoters, CMV promoters, or chicken 1-actin promoters combined with CMV enhancers (CAG promoters). The baculovirus-derived promoter is any of an IE1 promoter, an IE2 promoter, a p6.9 promoter, a VP39 promoter, and a p10 promoter. In a most preferred embodiment of the present disclosure, a polh promoter is employed to construct the recombinant viral construct of the present disclosure.

The recombinant baculoviral construct of the present disclosure, which serves as a transfer vector, is then co-transfected with a Bac-N-Blue viral DNA into an insect host cell. The Bac-N-Blue viral DNA provides the necessary viral backbone, which contains the propagation-essential genes of *Autographa californica* multiple nuclear polyhedrosis virus (AcMNPV). Homologous recombination between the recombinant baculoviral construct of the present disclosure and the Bac-N-Blue viral DNA in the insect host cell allows the generation of a recombinant virus, which is capable of propagating in the insect host cell and thereby producing the exogenous proteins respectively encoded by the three expression cassettes. The recombinant virus was further selected and purified by following the expression of the reporter polypeptide. Suitable insect host cell that may be used in the present disclosure includes, but is not limited to, *S. furgiperda* IPBL-9 (Sf9) cell, Sf21 cell, High Five cell, and Minic Sf9 cell. According to preferred embodiments of the present disclosure, the insect host cell is Sf21 cell.

This invention further encompasses a bi-subunit vaccine characterized in having the antigens produced by the recombinant viral construct of the present disclosure, in which two antigenic proteins (i.e., CSFV-E2 and PCV2-ORF2) and one immunomodulatory polypeptide (i.e., FIP-FVE) are simultaneously and efficiently expressed. The bi-subunit vaccine comprises:

a first effective amount of a CSFV antigen or a fragment thereof;

a second effective amount of a PCV2 antigen or a fragment thereof;

a third effective amount of an immunomodulatory polypeptide or a portion thereof; and a pharmaceutically acceptable adjuvant.

In some preferred embodiments of the present disclosure, the CSFV antigen is CSFV-E2, the PCV2 antigen is PCV2-ORF2, and the immunomodulatory polypeptide is FIP-FVE.

The following examples illustrate the identification of recombinant viral construct of the present invention and the use thereof in producing multiple antigens required for manufacturing a bi-subunit vaccine. The examples are illustrative only, and do not limit the scope of the present invention.

EXAMPLE

Materials and Methods

Cell Culture

Sf21 cells were cultured in TNM-FH medium containing 8-10% heat-inactivated fetal bovine serum (FBS) until a confluent cell monolayer was obtained.

Animal

The experimental procedures were approved by the Institutional Animal Care and Use Committee (IACUC) of Chung Yuan Christian University and conducted according to national animal welfare regulations.

Male BALB/c mice were purchased from AbKing Biotechnology and kept in an air-conditioned animal shelter at room temperature of 22° C. to 24° C. with controlled level of humidity (40% to 50%) in a 12-hour light-dark cycle. Each mouse weighed between 20 g to 25 g at the beginning of the test. Tap water and standard laboratory rodent chow were provided ad libitum.

Western Blot Analysis

After the cells were infected with recombinant viruses for 4 days, the proteins in the cell extracts were separated by SDS-PAGE according to the procedure of Laemmli on a mini ProteinIII system (Bio-Rad). The SDS-PAGE separated proteins were electro-transferred to a PVDF (polyvinyldiene difluoride) membrane (Millipore), which was then blocked with Tris-buffered saline (TTBS: 100 mM Tris, pH 7.4, 100 mM NaCl, and 0.1% Tween 20) containing 5% BSA (Sigma) at room temperature for 1 h with gentle shaking on an orbital shaker. Subsequently, membranes were incubated overnight at 4° C. with PBS-diluted anti-E2 antibody (1:2000), anti-PCV2 antibody (1:250), or anti-FVE antibody (1:250). Unbound antibodies were removed by three 5-min washes in TTBS buffer at room temperature with shaking. Membranes were then incubated with 1:2000 diluted horseradish peroxidase (HRP)-conjugated secondary antibodies for 1 hour at room temperature. The HRP on the membrane was detected by an enhanced chemiluminescence kit (Pierce) following the protocol provided by the manufacturer.

Enzyme-Linked Immunosorbent Assay (ELISA)

The extracts of cells infected with recombinant virus or purified recombinant sumo-PCV2 protein was diluted with phosphate-buffered saline (PBS) and added to a 96-well plate, followed by incubating at 4° C. overnight. The plate was blocked with PBS containing 5% (v/v) non-fat dry milk for 1-2 hours at room temperature. Next, the anti-PCV2 or anti-CSFV-E2 antibody in the serum was detected by incubating with mouse serum for another hour at room temperature. Unbound protein and antibodies were removed by washing three times with PBS containing 0.1% (V/V) Tween 20. The plate was then incubated with HRP conjugated-goat anti-mouse antibody for 30 minutes at room temperature. The HRP on the plate was detected by tetramethyl benzidine (TMB) substrate and the optical density (OD) at the wavelength of 490 nm was measured.

Example 1

Figure 1:
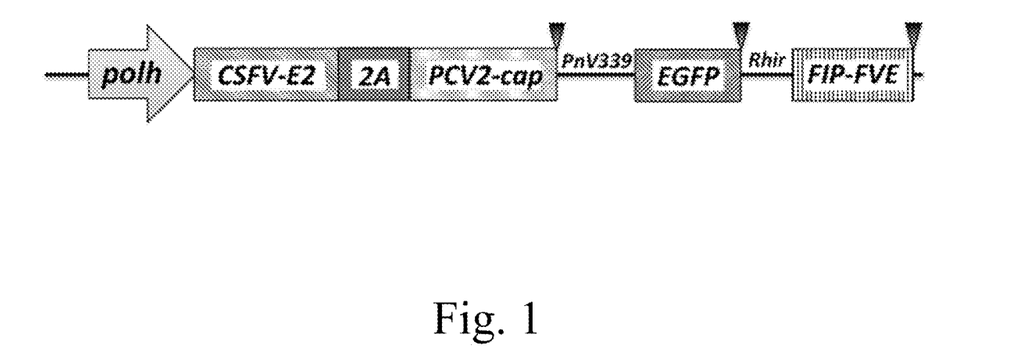
FIG. 1 is a schematic diagram of the recombinant viral construct constructed in according to example 1.1 of the present disclosure.

Generation of Recombinant Baculovirus 1.1 Construction of pBac-E2-2A-PCV2-PnV339-E-Rhir-FVE The exogenous CSFV-E2 gene, PCV2-cap gene, and FIP-FVE gene were respectively sub-cloned into the multiple cloning site (mcs) I, mcsII, and mcsIII of pBac-mcsI-2A-mcsII-PnV339-EGFP-Rhir-mcsIII cloning vector by restriction enzymes BamH I and Pst I (for CSFV-E2), Pst I (for PCV2-cap), and Spe I and Not I (for FIP-FVE). The resultant recombinant plasmid was named pBac-E2-2A-PCV2-PnV339-E-Rhir-FVE (FIG. 1).

1.2 Production of vAc-E2-2A-PCV2-PnV339-E-Rhir-FVE

Sf21 cells co-transfected with the recombinant plasmid pBac-E2-2A-PCV2-PnV339-E-Rhir-FVE of example 1.1 and Bac-N-Blue viral DNA (purchased from Invitrogen, USA) were incubated at 27° C. for 5 days to allow the homologous recombination between the plasmid and viral DNA.

The culture medium of the co-transfected cells that emitted green fluorescence due to the expression of EGFP was collected and used to conduct end point dilution with a ratio of 1:10 in another batch of Sf21 cells. The steps of collecting culture medium followed by conducting end point dilution in another batch of Sf21 cells were repeated 3-5 times until a single viral clone was obtained. A desired recombinant virus was eventually selected from a single viral plaque.

Example 2

Characterization of Recombinant Baculovirus of Example 1

The selected recombinant virus of example 1.2 was subjected to further analysis on its infectious and expression efficiency.

2.1 Detecting the Recombinant Baculovirus that May Express CSFV-E2, PCV2-ORF2, and/or FIP-FVE Proteins Via Following EGFP Expression Sf21 cells were respectively infected with (1) vAc-E2-PnV339-E-Rhir-mcsII, the recombinant baculovirus expressing CSFV-E2 protein; (2) vAc-PCV2-PnV339-E-Rhir-mcsII, the recombinant baculovirus expressing PCV2-ORF2 protein; (3) vAc-E2-PnV339-E-Rhir-FVE, the recombinant baculovirus expressing CSFV-E2 protein and FIP-FVE protein; and (4) vAc-E2-2A-PCV2-PnV339-E-Rhir-FVE, the recombinant baculovirus of example 1.2, which expressed three antigenic proteins simultaneously (i.e., CSFV-E2, PCV2-ORF2, and FIP-FVE) at the multiplicity of infection (moi) of 1. The recombinant viruses that may express the CSFV-E2, PCV2-ORF2 and FIP-FVE were followed by the expression of EGFP with the aid of a fluorescent microscope (view under FITC filter).

Figure 2:
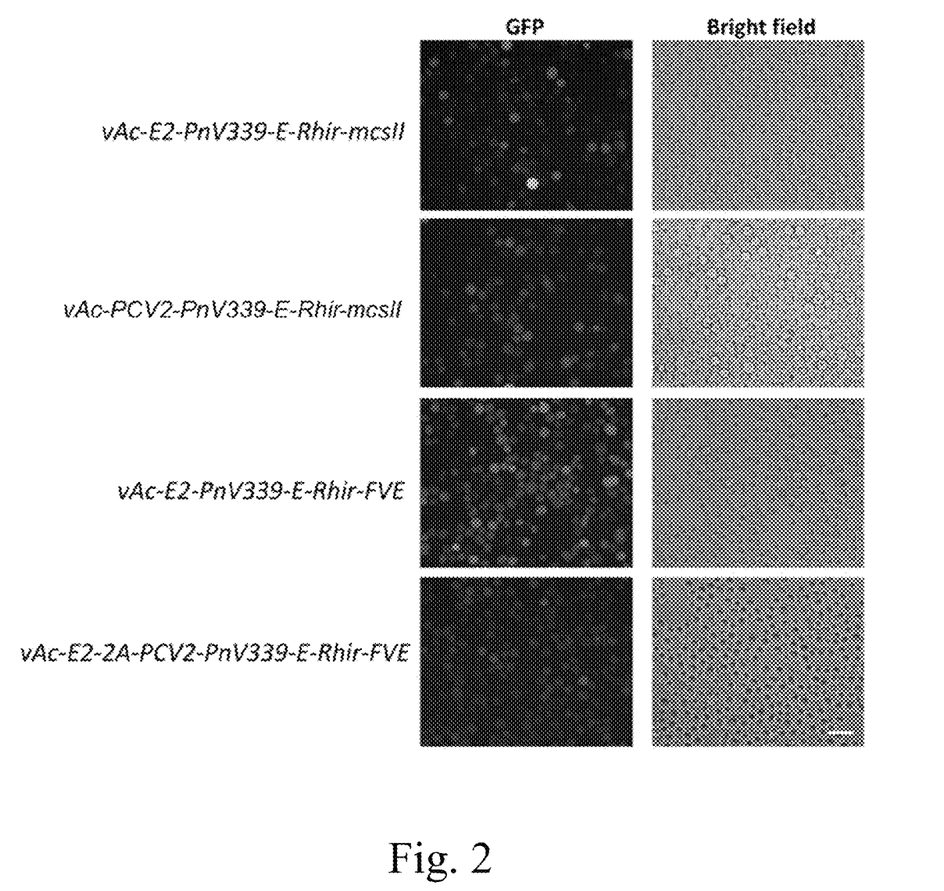
FIG. 2 are photographs of Sf21 cells infected with the specified recombinant baculovirus, the photographs were taken using FITC filter in according to example 2.1 of the present disclosure; the bar represents 50 µm.

The photographs in FIG. 2 indicate that cells infected with a recombinant virus that carried only one exogenous gene (i.e., vAc-E2-PnV339-E-Rhir-mcsII, or vAc-PCV2-PnV339-E-Rhir-mcsII), two exogenous genes (i.e., vAc-E2-PnV339-E-Rhir-FVE) or three exogenous genes (i.e., vAc-E2-2A-PCV2-PnV339-E-Rhir-FVE) would independently emit green fluorescence due to the expression of the EGFP reporter proteins.

2.2 Detecting the Expression of CSFV-E2, PCV2-ORF2, and FIP-FVE Antigens by Western Blot Analysis To further examine the expression of three exogenous genes carried by the recombinant virus, the individual protein expression was next confirmed by anti-E2, anti-PCV2, or anti-FVE antibody in a western blot assay. Briefly, Sf21 cells were respectively infected with (1) mock control, (2) vAc-E2-PnV339-E-Rhir-mcsII, (3) vAc-PCV2-PnV339-E-Rhir-mcsI, (4) vAc-E2-PnV339-E-Rhir-FVE, and (5) vAc-E2-2A-PCV2-PnV339-E-Rhir-FVE, at moi of 1. Four days post-infection, proteins extracted from the infected cells were analyzed by western blot analysis.

Figure 3A:
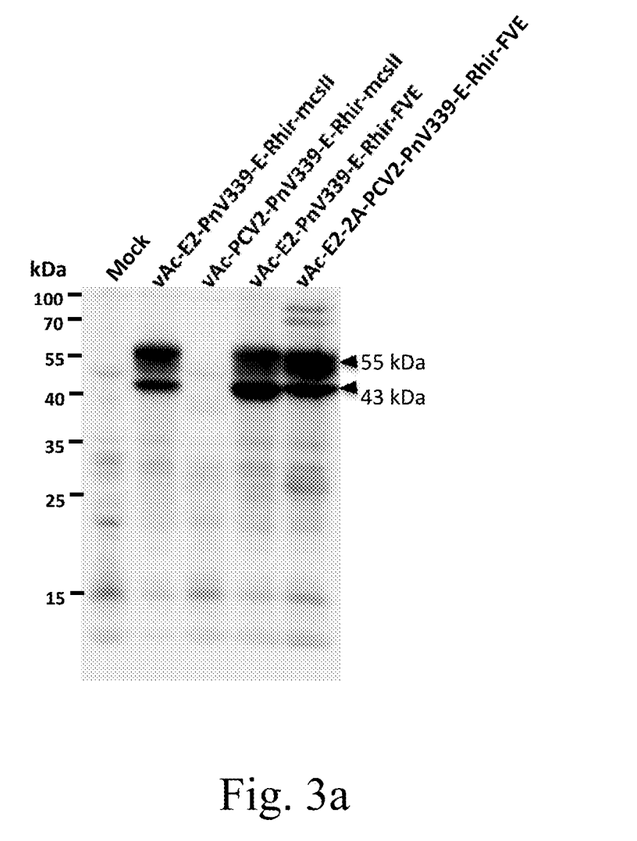
FIGS. 3a-3c are photographs depicting the western blot analysis of proteins extracted from Sf21 cells infected with specified recombinant baculovirus, wherein the proteins were respectively detected by (a) anti-E2 antibody, and the CSFV-E2 protein are approximately 43 kDa (non-glycosylated form) and 55 kDa (glycosylated form) as indicated by the arrow; (b) anti-PCV2 antibody, and the PCV2-ORF2 protein is approximately 26 kDa as indicated by the arrow; and (c) anti-FVE antibody, and the FIP-FVE protein is approximately 12.7 kDa as indicated by the arrow, in according to example 2.2 of the present disclosure.
Figure 3B:
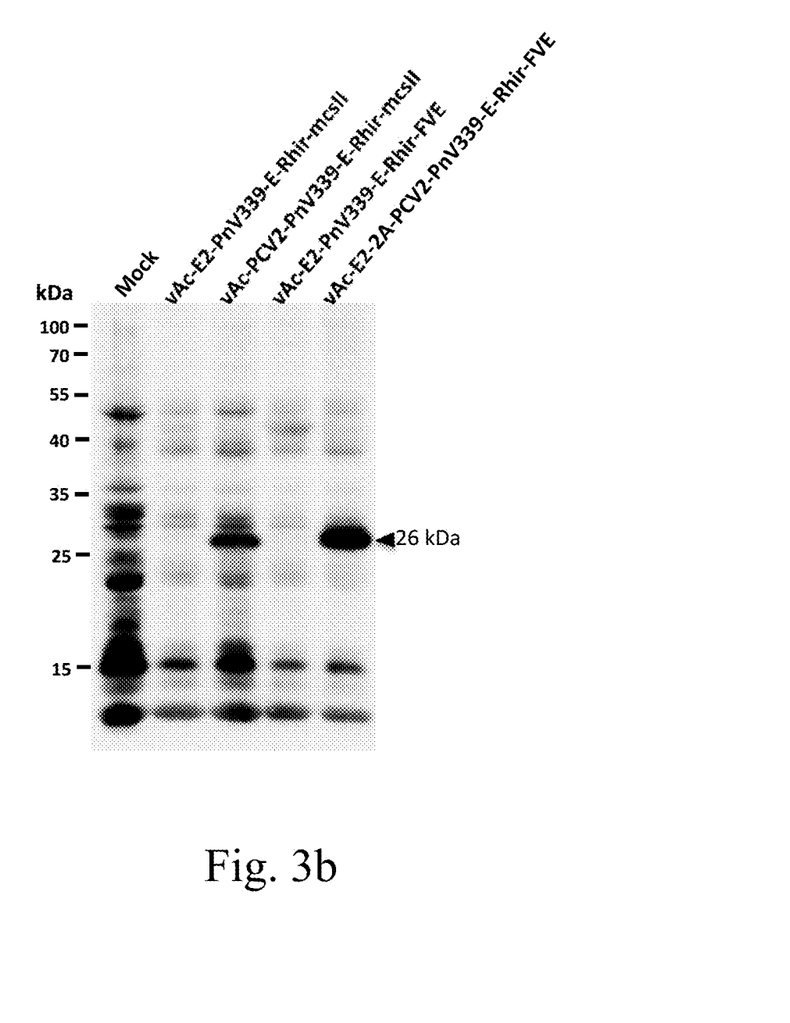
Figure 3C:
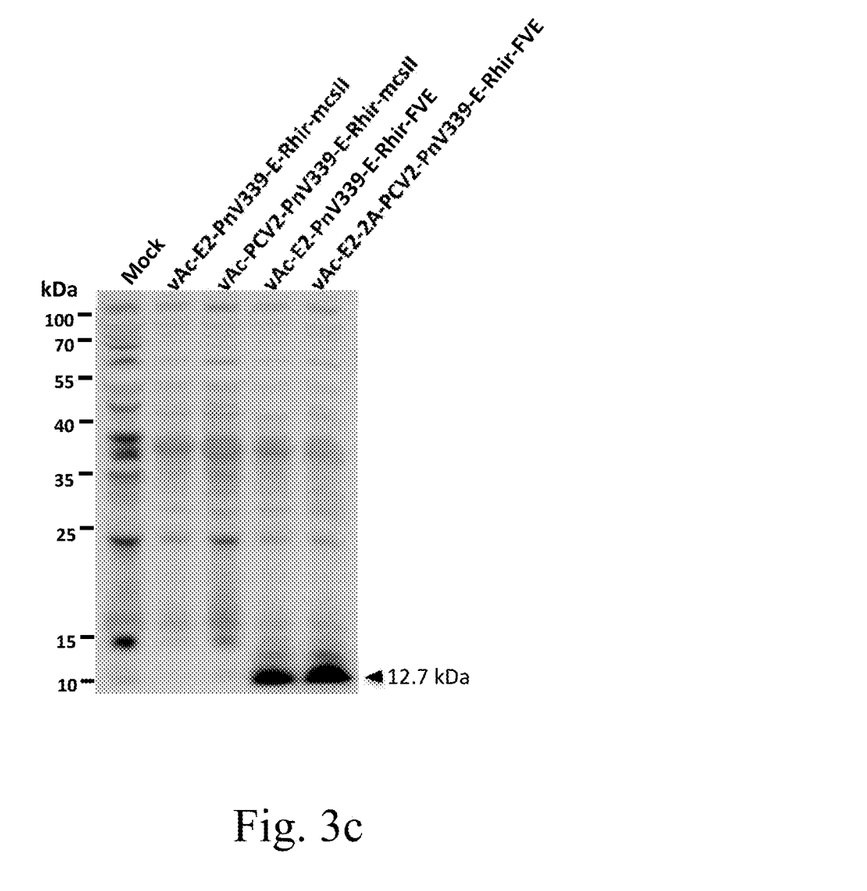

The data in FIG. 3 indicated that CSFV-E2 (FIG. 3a), PCV2-ORF2 (FIG. 3b), as well as FIP-FVE proteins (FIG. 3c) could be successfully expressed in the Sf21 cells infected by the recombinant virus of example 1.2 (i.e., vAc-E2-2A-PCV2-PnV339-E-Rhir-FVE). Furthermore, the expression levels of those proteins were similar among the various recombinant viruses tested. The simultaneous and efficient expression of two antigenic proteins and one immunomodulatory protein made the recombinant virus of example 1.2 a promising tool to produce multiple antigens required for a multiple-subunit vaccine of interest.

2.3 Detecting the Expression PCV2-ORF2 Proteins by Immunofluorescence Assay

Sf21 cells were seeding in 24-well plate and then infected by the recombinant virus at moi of 1. Four days post-infection, the EGFP expression was monitored under a microscope with a FITC filter. After discarding the culture medium, the plate was incubated at 27° C. for 1 hour. The cells were fixed by use of 100 µl of 4% paraformaldehyde, and were washed 4 times with PBS. 50 µl of methanol was added, followed by washing another 4 times with PBS. The cells were then blocked by use of 100 µl of 3% bovine serum albumin (BSA) with gently shaking for 1 hour, followed by further incubating with anti-PCV2 antibody (1:800) for 2 hours. After washing 5 times with PBS, the cells were labeled with rhodamine-conjugated anti-mouse secondary antibody (1:200) for another 2 hours. The PCV-2-expressing cells were examined using a confocal microscope under a rhodamine filter.

Figure 4:
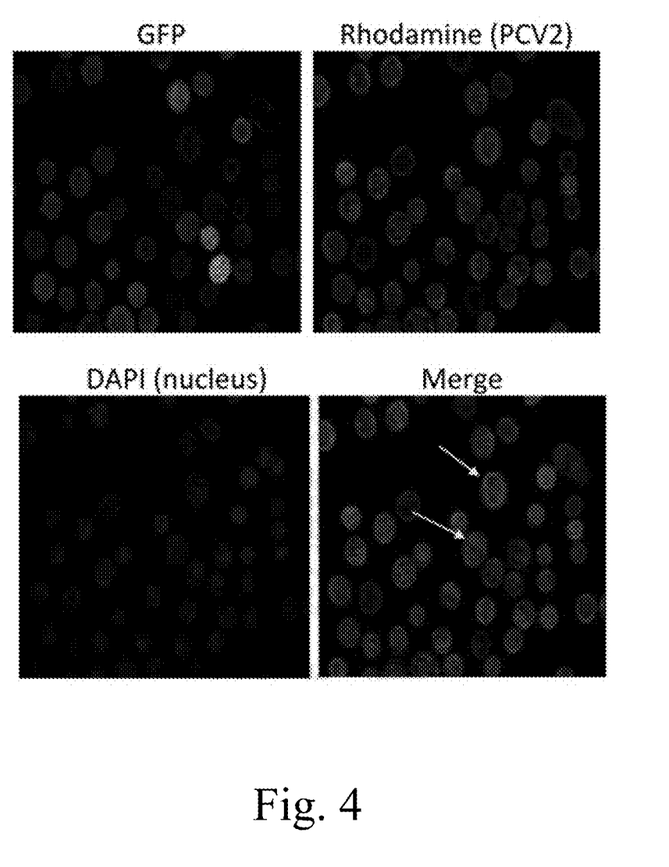
FIG. 4 are photographs of Sf21 cells infected with the recombinant baculovirus of example 1.2, the photographs were taken under FITC, rhodamine, or DAPI filter in according to example 2.3 of the present disclosure.

The merge image of Sf21 cells in FIG. 4 indicated that the cells infected with the recombinant virus simultaneously emitted green and red fluorescence due to the expression of EGFP and PCV2. The data combined with the western blot analysis indicated that the recombinant virus simultaneously and efficiently expressing the CSFV-E2, PCV2, and FIP-FVE proteins could serve as a bio-vector to generate multiple antigens required in a bi-subunit vaccine.

Example 3

Evaluating the In Vivo Immunogenicity of the Bi-Subunit Vaccine of the Present Disclosure In this example, a bi-subunit vaccine was formulated to comprise three antigens (i.e., CSFV-E2, PCV2-ORF2, and FIP-FVE, which were produced by the recombinant virus of example 1.2), in the presence or absence of an adjuvant (Freund's incomplete adjuvant, FIA); and the combined immunogenicity of the thus produced vaccine was evaluated.

Figure 5A:
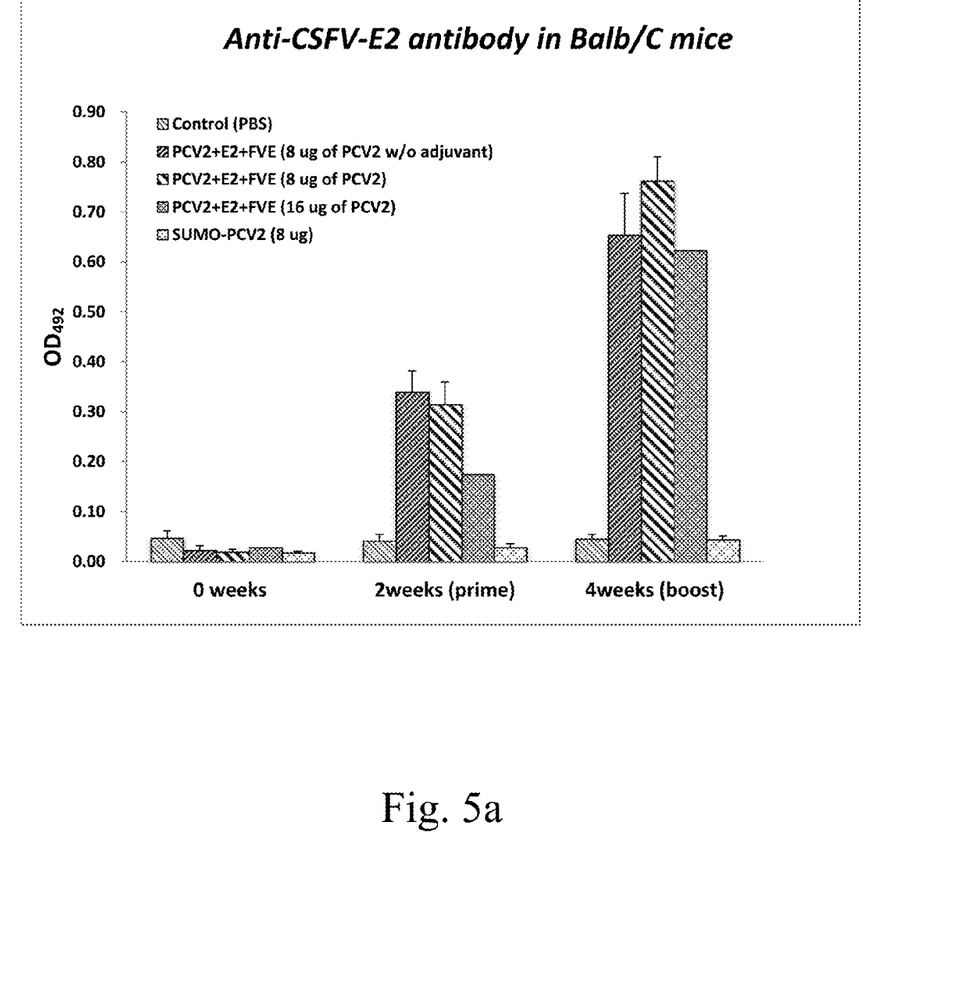
FIGS. 5a and 5b are photographs of enzyme-linked immunosorbent assay (ELISA) results depicting the levels of (a) anti-CSFV-E2 antibody, or (b) anti-PCV2-ORF2 antibody in serum of mice respectively immunized with the specified immunogens.
Figure 5B:
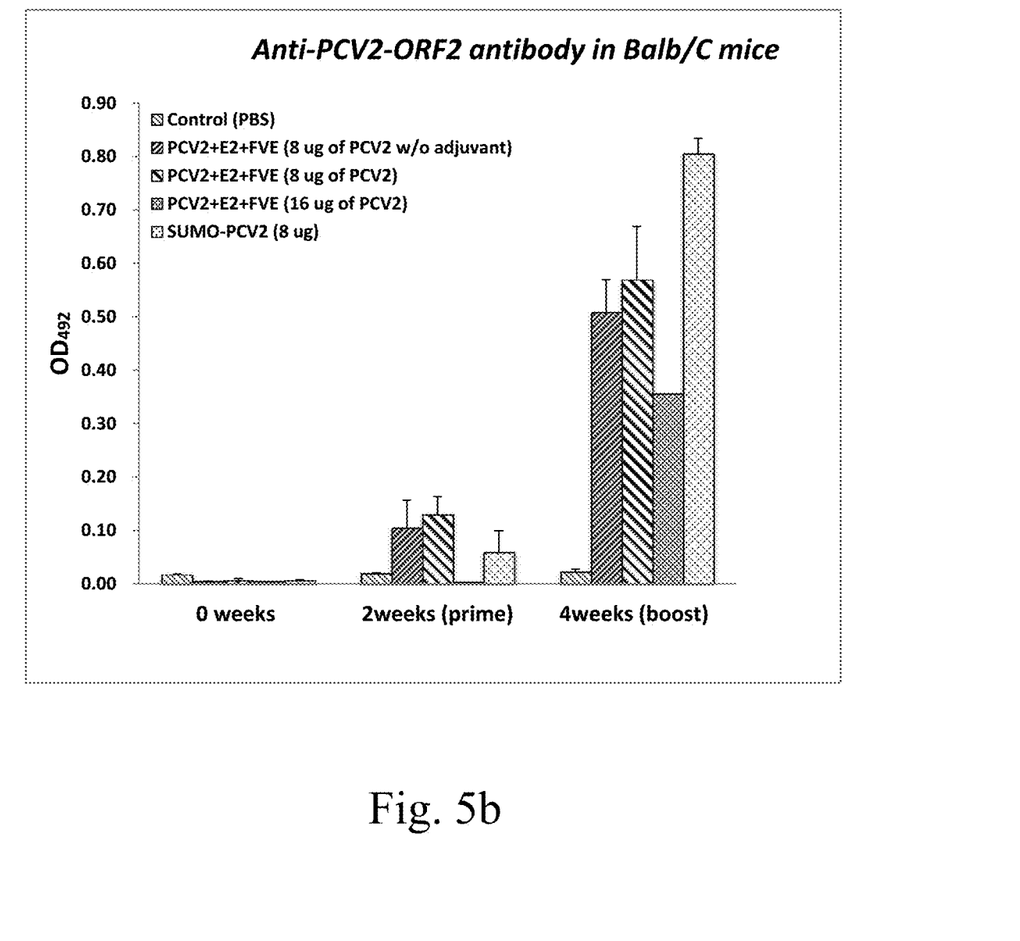

Male BALB/c mice were respectively immunized with PBS (group A), 8 µg of vaccine composition without adjuvant (group B), 8 µg of vaccine composition (group C), 16 µg of vaccine composition (group D), or 8 µg of recombinant sumo-PCV2 protein (group E). Each group consisted of 4 mice, and each mouse was immunized with two doses of treatments described above. The priming and boost were performed intraperitoneally on week 0 and week 2, respectively. To evaluate the immunogenicity of the treatments, serum sample were collected on weeks 0, 2, 4, and 6, respectively. Results were illustrated in FIG. 5.

The ELISA data of FIG. 5 indicated that 2-weeks after priming, both levels of anti-CSFV-E2 (FIG. 5a) and anti-PCV2-ORF2 antibodies (FIG. 5b) increased in the serum of mice treated with the vaccine, as compared to that of the PBS control group (or group A). The anti-PCV2 and anti-CSFV-E2 antibodies levels eventually reached a peak at week 4 (group B, C, and D). As a vaccination control, only anti-PCV2 antibody, but not anti-CSFV-E2 antibody, was detected in the serum of mice immunized with recombinant sumo-PCV2 protein (group E).

In sum, results from the foregoing working examples established that the novel recombinant viral construct of the present disclosure (i.e., vAc-E2-2A-PCV2-PnV339-E-Rhir-FVE) could simultaneously and efficiently express three exogenous proteins (i.e., CSFV-E2, PCV2-ORF2, and FIP-FVE), and this property makes the recombinant viral construct a useful bio-tool to produce multiple antigens necessary for producing a bi-subunit vaccine.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A recombinant viral construct for producing a bi-subunit vaccine, comprising,
a promoter;
a first expression cassette, operably linked to the promoter, wherein the first expression cassette comprises in sequence, a first nucleic acid encoding a classical swine fever virus (CSFV) antigen, a self-cleaving element encoding a self-cleaving peptide, and a second nucleic acid encoding a porcine circovirus type 2 (PCV2) antigen;
a second expression cassette, operably linked to the promoter, wherein the second expression cassette comprises in sequence, a first internal ribosomal entry site (IRES) element, and a third nucleic acid encoding a reporter polypeptide; and
a third expression cassette, operably linked to the promoter, wherein the third expression cassette comprises in sequence, a second IRES element, and a fourth nucleic acid encoding an immunomodulatory polypeptide;
wherein the CSFV antigen is CSFV-E2 and has an amino acid sequence of SEQ ID NO: 1; and the PCV2 antigen is PCV2 open reading frame 2 (ORF-2) and has an amino acid sequence of SEQ ID NO: 2.

2. The recombinant viral construct of claim 1, wherein the promoter is any of a polyhedrin (polh) promoter, a baculovirus-derived promoter, a Bombyx mori-derived actin promoter, a cytomegalovirus (CMV) promoter, or a chicken β-actin promoter combined with a CMV enhancer (CAG promoter).

3. The recombinant viral construct of claim 2, wherein the baculovirus-derived promoter is selected from the group consisting of an immediate-early1 (IE1) promoter, an IE2 promoter, a p6.9 promoter, a VP39 promoter, and a p10 promoter.

4. The recombinant viral construct of claim 1, wherein the self-cleaving peptide is selected from the group consisting of a nuclear inclusion protein a (Nia) protease, a P1 protease, a 3C protease, a L protease, a 2A protease, a 3C-like protease, and a 2A-like protease.

5. The recombinant viral construct of claim 4, wherein the self-cleaving peptide is the 2A-like protease.

6. The recombinant viral construct of claim 1, wherein each of the first and second IRES elements is derived from the 5' untranslated region (5'-UTR) of a virus selected from the group consisting of Perina nuda virus (PnV), Rhopalosiphum padi virus (RhPV), Aphid lethal paralysis virus, Black queen cell virus, Cricket paralysis virus, drosophila C virus, Himetobi P virus, Homalodisca coagulata virus-1, Kashmir bee virus, Plautia stali intestine virus, Solenopsis invicta virus-1, Taura syndrome virus, Encephalomyocarditis virus, and Hepatitis C virus.

7. The recombinant viral construct of claim 6, wherein each of the first and second IRES elements is independently selected from the group consisting of the PnV IRES having a nucleic acid sequence of SEQ ID NO: 5, and the RhPV IRES having a nucleic acid sequence of SEQ ID NO: 6.

8. The recombinant viral construct of claim 1, wherein the reporter polypeptide is selected from the group consisting of green fluorescence protein (GFPs), enhanced green fluorescence protein (EGFP), Discosoma sp. red fluorescent protein (DsRed), blue fluorescence protein (BFP), enhanced yellow fluorescent proteins (EYFP), Anemonia majano fluorescent protein (amFP), Zoanthus fluorescent protein (zFP), Discosoma fluorescent protein (dsFP), and Clavularia fluorescent protein (cFP).

9. The recombinant viral construct of claim 1, wherein the immunomodulatory polypeptide is any of fungal immunomodulatory protein Flammunlina velutipes (FIP-FVE), fungal immunomodulatory protein Ganodera tsugae (FIP-GTS), fungal immunomodulatory protein Volvariella volvacea (FIP-VVO), Ganoderma lucidum Ling-Zhi-8 (LZ-8), fungal immunomodulatory protein Ganoderma microsporum (GMI), or immunomodulatory Protein Tremella FuciFormis (TFP).

10. The recombinant viral construct of claim 9, wherein the immunomodulatory polypeptide is FIP-FVE and has an amino acid sequence of SEQ ID NO: 7.

11. The recombinant viral construct of claim 1, wherein the recombinant viral construct is derived from a baculovirus.

12. A bi-subunit vaccine comprising,
a first effective amount of a CSFV antigen,
a second effective amount of a PCV2 antigen;
a third effective amount of an immunomodulatory polypeptide, and
a pharmaceutically acceptable adjuvant;
wherein the CSFV antigen, the PCV2 antigen and the immunomodulatory polypeptide are produced by use of the recombinant viral construct of claim 1.

13. The bi-subunit vaccine of claim 12, wherein the CSFV antigen is CSFV-E2, the PCV2 antigen is PCV2-ORF2, and the immunomodulatory polypeptide is FIP-FVE.

* * * * *

SEQUENCE LISTING

<160> NUMBER OF SEQ ID NOS: 7

<210> SEQ ID NO 1
<211> LENGTH: 363
<212> TYPE: PRT
<213> ORGANISM: Artificial Sequence
<220> FEATURE:
<223> OTHER INFORMATION: CSFV-E2

<400> SEQUENCE: 1

```
Met Leu Arg Gly Gln Val Val Gln Gly Ile Ile Trp Leu Leu Leu Val
1               5                   10                  15

Thr Gly Ala Gln Gly Arg Leu Ser Cys Lys Glu Asp His Arg Tyr Ala
            20                  25                  30

Ile Ser Ser Thr Asn Glu Ile Gly Pro Leu Gly Ala Glu Gly Leu Thr
        35                  40                  45

Thr Thr Trp Lys Glu Tyr Asn His Gly Leu Gln Leu Asp Asp Gly Thr
    50                  55                  60

Val Arg Ala Ile Cys Ile Ala Gly Ser Phe Lys Val Thr Ala Leu Asn
65                  70                  75                  80

Val Val Ser Arg Arg Tyr Leu Ala Ser Leu His Lys Arg Ala Leu Pro
                85                  90                  95

Thr Ser Val Thr Phe Glu Leu Leu Phe Asp Gly Thr Ser Pro Ala Ile
            100                 105                 110

Glu Glu Met Gly Asp Asp Phe Gly Phe Gly Leu Cys Pro Phe Asp Thr
        115                 120                 125

Thr Pro Val Val Lys Gly Lys Tyr Asn Thr Thr Leu Leu Asn Gly Ser
    130                 135                 140

Ala Phe Tyr Leu Val Cys Pro Ile Gly Trp Thr Gly Val Ile Glu Cys
145                 150                 155                 160

Thr Ala Val Ser Pro Thr Thr Leu Arg Thr Glu Val Val Lys Thr Phe
                165                 170                 175

Lys Arg Glu Lys Pro Phe Pro His Arg Val Asp Cys Val Thr Thr Ile
            180                 185                 190

Val Glu Lys Glu Asp Leu Phe Tyr Cys Lys Leu Gly Gly Asn Trp Thr
        195                 200                 205

Cys Val Lys Gly Asn Pro Val Thr Tyr Thr Gly Gly Gln Val Arg Gln
    210                 215                 220

Cys Arg Trp Cys Gly Phe Asp Phe Lys Glu Pro Asp Gly Leu Pro His
225                 230                 235                 240
```

```
Tyr Pro Ile Gly Lys Cys Ile Leu Ala Asn Glu Thr Gly Tyr Arg Val
            245                 250                 255

Val Asp Ser Thr Asp Cys Asn Arg Asp Gly Val Val Ile Ser Thr Glu
        260                 265                 270

Gly Glu His Glu Cys Leu Ile Gly Asn Thr Thr Val Lys Val His Ala
            275                 280                 285

Leu Asp Gly Arg Leu Ala Pro Met Pro Cys Arg Pro Lys Glu Ile Val
        290                 295                 300

Ser Ser Ala Gly Pro Val Arg Lys Thr Ser Cys Thr Phe Asn Tyr Thr
305                 310                 315                 320

Lys Thr Leu Arg Asn Lys Tyr Tyr Glu Pro Arg Asp Ser Tyr Phe Gln
            325                 330                 335

Gln Tyr Met Leu Lys Gly Glu Tyr Gln Tyr Trp Phe Asp Leu Asp Val
            340                 345                 350

Thr Asp His His Thr Asp Tyr Phe Ala Glu Phe
            355                 360

<210> SEQ ID NO 2
<211> LENGTH: 468
<212> TYPE: PRT
<213> ORGANISM: Artificial Sequence
<220> FEATURE:
<223> OTHER INFORMATION: PCV2-ORF2

<400> SEQUENCE: 2

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Ile Lys Arg Thr Thr Val Lys Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro Lys Met Thr Tyr Pro Arg Arg
225                 230                 235                 240
```

```
Arg Tyr Arg Arg Arg His Arg Pro Arg Ser His Leu Gly Gln Ile
            245                 250                 255

Leu Arg Arg Pro Trp Leu Val His Pro Arg His Arg Tyr Arg Trp
        260                 265                 270

Arg Arg Lys Asn Gly Ile Phe Asn Thr Arg Leu Ser Arg Thr Phe Gly
    275                 280                 285

Tyr Thr Ile Lys Arg Thr Thr Val Lys Thr Pro Ser Trp Ala Val Asp
    290                 295                 300

Met Met Arg Phe Asn Ile Asn Asp Phe Leu Pro Gly Gly Gly Ser
305                 310                 315                 320

Asn Pro Arg Ser Val Pro Phe Glu Tyr Tyr Arg Ile Arg Lys Val Lys
                325                 330                 335

Val Glu Phe Trp Pro Cys Ser Pro Ile Thr Gln Gly Asp Arg Gly Val
                340                 345                 350

Gly Ser Ser Ala Val Ile Leu Asp Asp Asn Phe Val Thr Lys Ala Thr
            355                 360                 365

Ala Leu Thr Tyr Asp Pro Tyr Val Asn Tyr Ser Ser Arg His Thr Ile
        370                 375                 380

Thr Gln Pro Phe Ser Tyr His Ser Arg Tyr Phe Thr Pro Lys Pro Val
385                 390                 395                 400

Leu Asp Ser Thr Ile Asp Tyr Phe Gln Pro Asn Asn Lys Arg Asn Gln
                405                 410                 415

Leu Trp Leu Arg Leu Gln Thr Ala Gly Asn Val Asp His Val Gly Leu
            420                 425                 430

Gly Thr Ala Phe Glu Asn Ser Ile Tyr Asp Gln Glu Tyr Asn Ile Arg
        435                 440                 445

Val Thr Met Tyr Val Gln Phe Arg Glu Phe Asn Leu Lys Asp Pro Pro
    450                 455                 460

Leu Asn Pro Lys
465

<210> SEQ ID NO 3
<211> LENGTH: 20
<212> TYPE: PRT
<213> ORGANISM: Artificial Sequence
<220> FEATURE:
<223> OTHER INFORMATION: 2A-like protease-1

<400> SEQUENCE: 3

Ala Gln Gly Trp Val Pro Asp Leu Thr Val Asp Gly Asp Val Glu Ser
1               5                   10                  15

Asn Pro Gly Pro
            20

<210> SEQ ID NO 4
<211> LENGTH: 20
<212> TYPE: PRT
<213> ORGANISM: Artificial Sequence
<220> FEATURE:
<223> OTHER INFORMATION: 2A-like sequence-2

<400> SEQUENCE: 4

Ile Gly Gly Gly Gln Lys Asp Leu Thr Gln Asp Gly Asp Ile Glu Ser
1               5                   10                  15

Asn Pro Gly Pro
            20

<210> SEQ ID NO 5
```

-continued

<211> LENGTH: 339
<212> TYPE: DNA
<213> ORGANISM: Artificial Sequence
<220> FEATURE:
<223> OTHER INFORMATION: PnV IRES

<400> SEQUENCE: 5

```
ttgtggcact ggcttggatc tcccttacac atgtgattac atgatagact tattagtagt      60
agatacatct aaattctaca acgacctagt aagtattagt tatgtgaaat agaatgtgga     120
ggattttaaa ttgtgaatag gcctttatat tcggagtagg tagtattgcg tatactatta     180
atcccacaat acgtggtctc cgtcttagta tttttaattt gcgccccaat ggaaatggct     240
cttcggactt gagtacagag gggcaaccca taaatgatga ttaacccaca acaattatgt     300
aagaaaacac tttctgacga actttgcgat cgcacggat                            339
```

<210> SEQ ID NO 6
<211> LENGTH: 579
<212> TYPE: DNA
<213> ORGANISM: Artificial Sequence
<220> FEATURE:
<223> OTHER INFORMATION: RhPV IRES

<400> SEQUENCE: 6

```
gataaagaa cctataatcc cttcgcacac cgcgtcacac cgcgctatat gctgctcatt       60
aggaattacg gctcctttt tgtggataca atctcttgta tacgatatac ttattgttaa     120
tttcattgac ctttacgcaa tcctgcgtaa atgctggtat agggtgtact tcggatttcc     180
gagcctatat tggttttgaa aggacctta agtccctact atactacatt gtactagcgt     240
aggccacgta ggcccgtaag atattataac tattttatta tatttattc accccccaca     300
ttaatcccag ttaaagcttt ataactataa gtaagccgtg ccgaaacgtt aatcggtcgc     360
tagttgcgta acaactgtta gtttaatttt ccaaaattta ttttcacaa ttttagtta     420
agatttagc ttgccttaag cagtctttat atcttctgta tattatttta agtttatag     480
gagcaaagtt cgctttactc gcaatagcta ttttatttat tttaggaata ttatcacctc     540
gtaattattt aattataaca ttagctttat ctatttata                            579
```

<210> SEQ ID NO 7
<211> LENGTH: 115
<212> TYPE: PRT
<213> ORGANISM: Artificial Sequence
<220> FEATURE:
<223> OTHER INFORMATION: FIP-FVE

<400> SEQUENCE: 7

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95
```

```
Val Ile Pro Asp Thr Gly Asn Ser Glu Glu Tyr Ile Ile Ala Glu Trp
            100                 105                 110

Lys Lys Thr
        115
```